US012583890B2

(12) United States Patent
Wang

(10) Patent No.: US 12,583,890 B2
(45) Date of Patent: Mar. 24, 2026

(54) METHODS FOR CONTROL OF AN INFECTIVE DISEASE WITH A VACCINE

(71) Applicant: RUSSELLVILLE CARDIOLOGY CONSULTANTS, P.A., Russellville, AR (US)

(72) Inventor: Dai Yuan Wang, Russellville, AR (US)

(73) Assignee: RUSSELLVILLE CARDIOLOGY CONSULTANTS, P.A., Russellville, AR (US)

( * ) Notice: Subject to any disclaimer, the term of this patent is extended or adjusted under 35 U.S.C. 154(b) by 724 days.

(21) Appl. No.: 17/948,406

(22) Filed: Sep. 20, 2022

(65) Prior Publication Data

US 2023/0374080 A1     Nov. 23, 2023

Related U.S. Application Data

(60) Provisional application No. 63/344,421, filed on May 20, 2022.

(51) Int. Cl.
*A61K 39/00*     (2006.01)
*C07K 14/165*     (2006.01)

(52) U.S. Cl.
CPC ...... *C07K 14/165* (2013.01); *A61K 2039/545* (2013.01); *C12N 2770/20031* (2013.01); *C12N 2770/20043* (2013.01)

(58) Field of Classification Search
None
See application file for complete search history.

(56) References Cited

PUBLICATIONS

Voysey et al. (Lancet 2021; 397: 99-111). (Year: 2021).*
Billeskov et al. (Human Vaccines & Immunotherapeutics, 2019, vol. 15, No. 2, 407-411). (Year: 2019).*
Roozen et al. (Lancet Glob Health 2022; 10: e570-73). (Year: 2022).*
Kathy Katellaf, Omicron, Delta, Alpha, and More: What To Know About the Coronavirus Variants. Yale Medicine (Mar. 30, 2022), www.yalemedicine.org/news/covid-19-variants-of-concern-omicron.
Nick Andrews et al., Covid-19 Vaccine Effectiveness against the Omicron (B.1.1.529) Variant. 386 N. Engl. J. Med. 1532-1546 (2022).
Michelle Roberts, Oxford/AstraZeneca Covid vaccine 'dose error' explained, BBC News (Nov. 27, 2020, www.bbc.com/news/health-55086927).

* cited by examiner

*Primary Examiner* — Zachary S Skelding
(74) *Attorney, Agent, or Firm* — troutman pepper locke; Tim Tingkang Xia, Esq.

(57) ABSTRACT

The COVID-19 pandemic has led to a worldwide health crisis and devastating economic and social issues. The present invention provides a method enhancing the effectiveness of the vaccines currently used for the severe acute respiratory syndrome coronavirus 2 (SARS-CoV-2), which comprises three incremental doses of a vaccine to elicit an enhanced immune response against in a subject. The first dose, second dose, and final dose are administered in the amount of 10-25%, 45-55%, and about 100% of the vaccine's full-strength dose, respectively.

13 Claims, 3 Drawing Sheets

METHODS FOR CONTROL OF AN INFECTIVE DISEASE WITH A VACCINE

CROSS-REFERENCE TO RELATED PATENT APPLICATION

This application claims priority to and the benefit of U.S. Provisional Patent Application Ser. No. 63/344,421, filed on May 20, 2022, which is incorporated herein in its entirety by reference.

FIELD OF THE INVENTION

The present disclosure relates generally to field of immunology, and more particularly to a vaccine administering method eliciting an immune response against an antigen or a microorganism, e.g., virus, bacteria, and etc.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Vaccines have been a crucial public health tool for decades, however, their durability are not well understood. For most of the vaccines, their protection against antigens may last for a certain period a time, from a few days to a few years or even for life. For public health, long and high effectiveness of vaccines against severe disease and death is critically important. For example, during the two years of COVID-19 pandemic, the vaccines for COVID-19 have contributed significantly to bring the pandemic under control. However, the vaccines for COVID-19 are not as effective as expected, especially the vaccines derived from the inactivated and killed virus. To address this effectiveness reduction, boost doses of the vaccines have been used, but their effectiveness were less than expected due to new variants produced by mutations of the virus (1, 2, 3). Due to the new variants of the COVID-19 virus, the pandemic keeps spreading worldwide.

The COVID-19 vaccine booster dose is administered in an equivalent dose both 2-3 weeks and several months after the initial dose (5). This long interval between doses gives the virus a time window to mutate and potentially cause immune escape, reducing the vaccine's effectiveness.

Therefore, there remains an imperative need for a method to enhance the efficacy and/or effectiveness of the vaccines, e.g. vaccines against COVID-19, in terms of their strength and protection duration.

SUMMARY OF THE INVENTION

The invention is related to using a vaccine in an incremental schedule to produce a better immune reaction. It consists of administering a low priming dose of a vaccine followed by a higher dose or doses in short time intervals, which will improve the effectiveness of the vaccine and prevent severe infection by the virus in humans. It will also shorten the time window for the possibility of mutation of the virus, which prevents or stops a pandemic. It will also prevent large number of the individuals being infected in the population, which will allow the virus to duplicate in a large quantity and increase the possibility for the mutation of the virus. This will limit the space for the mutation of the virus and, furthermore, prevent or stop the pandemic. The invention is based on the observation that a half dose is better than a full dose of a COVID-19 vaccine in inducing immune response, and the introduction of the second and third doses of the vaccine produces stronger immune responses than the first one.

In one aspect of the invention, a method for enhancing an immune response to a coronavirus in a subject, comprising (1) administering to the subject a first dose of a coronavirus vaccine in the amount of 10-25% of the vaccine's full-strength dose on Day 1 of an administering schedule; (2) administering to the subject a second dose of the coronavirus vaccine in the amount of 45-55% of the vaccine's full-strength between Day 4-22 of the administering schedule; and (3) administering to said subject a final dose of the coronavirus vaccine in the amount of 80-100% of said vaccine's full-strength on the last day of the administering schedule; wherein the immune response produced in the subject is stronger than, and/or lasts longer than the immune response produced in the subject if the full-strength dose is given two or three times over the same length of time of the administering schedule.

In one embodiment, the coronavirus is severe acute respiratory syndrome coronavirus 2 (SARS-CoV-2).

In one embodiment, the coronavirus vaccine is an inactivated virus vaccine.

In one embodiment, the coronavirus vaccine is an mRNA vaccine.

In one embodiment, the administering schedule lasts about 24-32 days.

In one embodiment, the administering schedule lasts 28 days.

In one embodiment, the second dose is administered on Day 14 of the administering schedule, and the final dose is administered on Day 28 of the administering schedule.

In one embodiment, a third dose is administered between the second dose and the final dose, and wherein the third dose contains approximately about 50-70% of the vaccine's full-strength dose.

In one embodiment, the second dose and the third dose are administered on two separate days which equally divide the time period between the Day 1 and last day of the administering schedule.

In one embodiment, the first dose contains 10% of said vaccine's full-strength dose.

In one embodiment, the second dose contains 50% of said vaccine's full-strength dose.

In one embodiment, the final dose contains 100% of said vaccine's full-strength dose.

In another aspect of the invention, a method for enhancing an immune response to SARS-CoV-2 in a subject, comprising (1) administering to the subject a first dose of a SARS-CoV-2 vaccine in the amount of 10% of the vaccine's full-strength dose on Day 1 of an administering schedule; (2) administering to the subject a second dose of the SARS-CoV-2 vaccine in the amount of 50% of the vaccine's full-strength on about Day 14 of the administering schedule; and (3) administering to said subject a final dose of the SARS-CoV-2 vaccine in the amount of 100% of said vaccine's full-strength on the Day 28 of the administering schedule; wherein the immune response produced in the subject is stronger than, and/or lasts longer than the immune response produced in the subject if the full-strength dose is given two or three times over the same length of time of the administering schedule; wherein the SARS-CoV-2 vaccine is an inactivated virus vaccine.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE FIGURES

Illustrative embodiments of the invention will hereafter be described with reference to the accompanying drawings, wherein like numerals denote like elements.

DETAILED DESCRIPTION OF THE INVENTION

Figure 1:
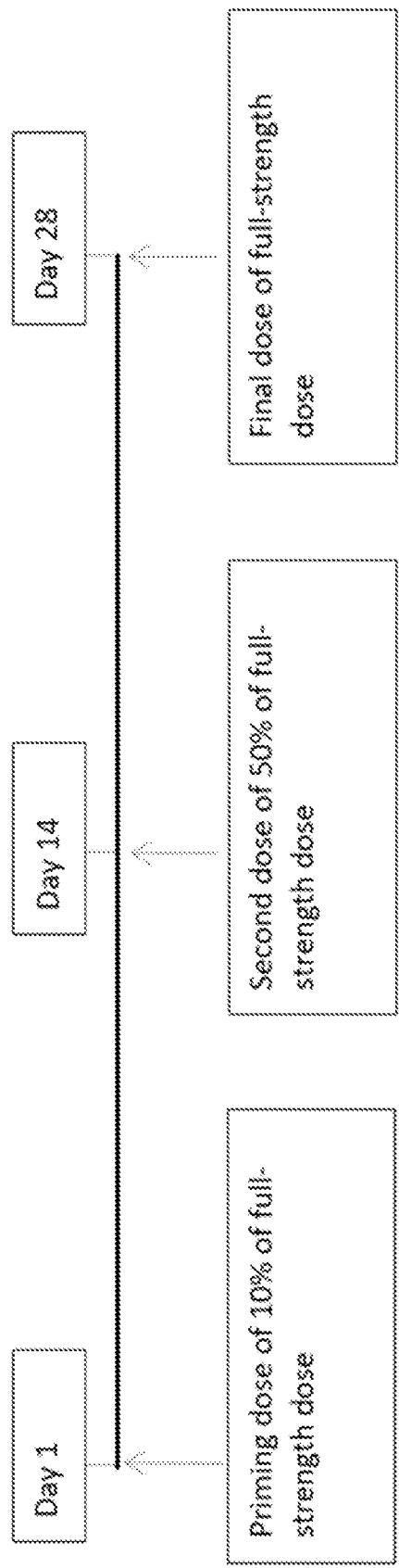
FIG. 1 illustrates an incremental dose schedule of SINO-PHARM's BBIBP-CorV vaccine.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of "a", "an", and "the" includes plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper,"

depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising", or "includes" and/or "including", or "has" and/or "having", or "carry" and/or "carrying", or "contain" and/or "containing", or "involve" and/or "involving", "characterized by", and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in the disclosure, the phrase "at least one of A, B, and C" should be construed to mean a logical (A or B or C), using a non-exclusive logical OR. As used herein, the term "and/or" includes any and all combinations of one or more of the associated listed items.

As used in the disclosure, "adjuvant" means a pharmaceutically acceptable substance or composition that increases the immune response to an antigen.

As used in the disclosure, "administering schedule" refers to a time schedule during a certain period for administering more than one dose of a vaccine. An administering schedule may last between 15-40 days, during which more than one dose of a vaccine are administered to a subject in a sequential order.

As used in the disclosure, "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

As used in the disclosure, "antigen" or "immunogen" refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to killed, attenuated or inactivated bacteria or viruses. The term antigen also refers to antibodies, such as anti-idiotype antibodies or fragments thereof, and to synthetic peptide mimotopes that can mimic an antigen or antigenic determinant (epitope).

As used in the disclosure, "excipient" refers to any component of a vaccine that is not an antigen.

As used in the disclosure, "dose" or "dosage" refers to physically discrete units suitable for use in a subject, each unit containing a predetermined-quantity of a vaccine or immunogenic composition calculated to produce the desired responses, i.e., the immune response. The quantity to be administered, both according to number of treatments and unit dose, depends on the protection or effect desired. A "first dose" or "priming vaccine" refers to the dose of such a composition given on Day 1. A "second dose", a "third dose", a "fourth dose", a "fifth dose", or a "final dose" refers to an amount of such composition given subsequent to the first dose, which may or may not be the same vaccine or immunogenic composition as the first dose.

As used in the disclosure, "full strength dose" refers to a dose or dosage administered to a subject in a single administration traditionally used in clinical settings. The SINOPHARM SARS-CoV-2 vaccine's full-strength dose is 600 SU, while the Pfizer SARS-CoV-2 mRNA vaccine's full-strength dose is 100 unites.

As used in the disclosure, "immune response" in a subject refers to the development of a humoral immune response, a cellular immune response, or a humoral and a cellular immune response to an antigen. A "humoral immune response" refers to one that is mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

As used in the disclosure, "immunologically protective amount" or "effective amount" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

As used in the disclosure, "immunogenic" means evoking an immune response or antigenic. Thus an immunogenic composition would be any composition that induces an immune response.

As used in the disclosure, "Day N" refers, respectively, to any time on the N th day of the administering time schedule. For example, vaccinating a subject with a second vaccine on Day 14 means that the second vaccine is administered at any time on the 14th day of the administering schedule, or 13 days after the 1st day of the administering schedule.

As used in the disclosure, "pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

As used in the disclosure, "Sinopharm COVID-19 (BBIBP-CorV, COVILO)" is an inactivated vaccine made of virus particles grown in culture and lacks the disease-producing capability. This vaccine was developed by China National Pharmaceutical Group Co., Ltd. (Sinopharm) and the Beijing Institute of Biological Products Co in 2020.

As used in the disclosure, the expression "a subject in need thereof" means a human or a non-human animal that is susceptible to and/or is in need of preventive protection from a microbial (e.g., bacterial or viral) infection. In the context of the invention, the term "subject" includes a subject that is susceptible to an infection selected from the group consisting of pertussis, diphtheria, tetanus, tuberculosis, malaria, anthrax, cholera, typhoid, leprosy, Lyme's disease, streptococcal infection, *E. coli* infection, staphylococcal infection, plague, clostridial infection, meningococcal infection, pneumococcal infection, pneumonia, meningitis, sepsis, influenza, chickenpox, HIV infection, RSV infection, polio, small pox, rabies, rotavirus infection, papillomas, cervical cancer, Ebola, hepatitis, yellow fever, measles, mumps, Rubella infection and coronavirus infection.

As used in the disclosure, in certain embodiment, the term "subject" includes a child who is 3 years old. For example, the present methods may be used for infants who are less than 1 month, about 1 month, about 2 months, about 3 months, about 4 months, about 5 months, about 6 months, about 7 months, about 8 months, about 9 months, about 10 months, about 11 months or about 12 months old. In other embodiments, the methods of the present invention may be used to treat children who are about 1 year old, less than 1 year old, less than 2 years old, less than 3 years, less than 4 years, less than 5 years, less than 6 years, less than 7 years, less than 8 years, less than 9 years, less than 10 years, less than 11 years, less than 12 years, less than 13 years, less than 14 years, or less than 15 years old. In certain embodiments, the methods of the present invention may be used to treat adolescents who are about 15 years old, about 16 years old, about 17 years old, about 18 years old, about 19 years old, about 20 years old or less than 20 years old.

In certain embodiments, the term "subject" includes an adult more than 50 years old, more than 55 years old, more than 60 years old, more than 65 years old, more than 70 years old or more than 75 years old.

In certain embodiments, the term "subject" includes an adult more than 20 years old, more than 25 years old, more than 30 years old, more than 35 years old, more than 40 years old, more than 45 years old or more than 50 years old. In certain embodiments, the adult is not pre-immunized with a vaccine such as tetanus vaccine, diphtheria vaccine, or pertussis vaccine.

In certain embodiments, the term "subject" includes an adult or adolescent more than 10 years of age who has been immunized with a vaccine, but needs to get a booster dose of the vaccine. In certain embodiments, the term includes an adult who may have been pre-immunized but has developed compromised immunity to an infection and needs to receive an additional vaccine dose (e.g., a booster dose). In certain embodiments, the term "subject" includes subjects that are allergic to one or more components of a vaccine. In a further embodiment, the term includes subjects that may be at an increased risk of developing an allergic response to a vaccine.

As used in the disclosure, the term "to enhance the efficacy, effectiveness, and/or protection duration of a vaccine" refers to increased protection and/or increased duration of protection afforded by administration of a vaccine in an incremental schedule of the present invention, as compared to administration of the vaccine according to any traditional administering schedule. In certain embodiments, the term includes one or more of the following: (a) prevention of disease due to a pathogenic bacterium or virus; (b) decreased bacterial or viral titers in the infected host or decreased pathogen load in infected host; (c) faster clearance of pathogen from infected host; (d) increased production of pathogen-specific Th1 type IgG isotype titers; (e) reduced or abrogated allergic response due to vaccine administration; (f) reduced or abrogated production of serum IgE in the host due to vaccine administration; (g) reduction in Th2 response; (h) decreased production of pathogen-specific Th2 type IgG isotype titers; (i) decrease in the number of vaccine doses required for protection; (j) prevention of infection and transmission of pathogen and/or infectious disease; and/or (k) long-lasting (durable) resistance to subsequent pathogen challenge, as compared to a subject administered with a vaccine according to any traditional administering schedule. In certain embodiments, the term includes enhancing the safety of a vaccine.

As used in the disclosure, "therapeutically effective amount," in the context of this disclosure, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular virus used, or the condition of the subject, and can be determined by a veterinary physician.

As used in the disclosure, "treating" refers to preventing a disorder, condition, or disease to which such term applies; or to preventing one or more symptoms of such disorder, condition, or disease; or to reversing, alleviating, or inhibiting the progress of such disorder, condition, or disease.

As used in the disclosure, "treatment" refers to the act of "treating" as defined above.

As used in the disclosure, "vaccine" refers to a composition that includes an antigen, as defined herein. Administration of the vaccine to a subject results in an immune response, generally against one or more specific diseases. The amount of a vaccine that is therapeutically effective may vary depending on the particular virus used, or the condition of the dog, and can be determined by a veterinary physician. The vaccine may be introduced directly into the subject by the subcutaneous, oral, oronasal, or intranasal routes of administration.

The present invention is directed to a vaccine administering method which enhances the efficacy, effectiveness, and/or protection duration of the vaccine. The method includes administering a low priming dose of a vaccine (first dose) followed by a higher dose or doses (second and final dose) in short time intervals, which improves the efficacy and/or effectiveness of the vaccine and prevents severe infection by the virus in humans. It also lowers the possibility of mutation of the virus, which may produce variants, prolonging a pandemic.

The vaccines introduce antigens of the virus into the human body to trigger immunoreaction of the body against the antigens. When a micronism containing the same or similar antigens enters the body, the immune system recognizes it and launches immunoreaction against it. Accordingly, the vaccines prevent the invading microorganisms from duplicating in the body and causing damage. The vaccine also decreases the possibility of mutation of the microorganisms to new variants, which are potentially more contiguous and pathogenic. Such mutations only happen during the duplication of the virus. RNA viruses, like the coronavirus, are more prone to these mutations because they are single-chain viruses.

The vaccine will not prevent the virus from entering the human body. However, the immune system of vaccinated humans will recognize the virus and prevent it from duplicating in the body.

When the virus infects a large percentage of the population, it may immunize most people. The pandemic will stop with so-called population immunity. However, the population immunity has a significant cost of the public health, because, to attain the population immunity, a large number of vulnerable population, e.g. individuals without contact to the virus, some of them would be severely sick or even die during the pandemic.

The global pandemic provides time and space for viruses to mutate and produce new variants since the mutation of the virus will occur in the human body where it duplicates. It is especially true in those severely sick individuals, where the virus will duplicate in a very large quantity. Meanwhile, the population may also lose its immunity acquired from the original strain of the virus.

Therefore, from this perspective, the killed or inactivated vaccine provides a more comprehensive protection because it contains a plurality or most of antigens of the virus, if not all of them. In practice, however, the efficacy and/or effectiveness of the killed or inactivated virus is not as good as that of the mRNA vaccine. Despite of this, the mRNA vaccine seems less effective in combatting new variants of some virus, e.g. the SARS-CoV-2.

In general, each mutation of the virus may create a unique antigen, e.g. a structurally different Spike protein. These mutations may induce the mRNA vaccine becoming less effective, if not becoming ineffective at all. The killed or inactivated virus vaccine contains a plurality or most of antigens of the virus, while mRNA vaccine may contain mRNA sequence of a single antigen of the virus. Thus, the killed or inactivated virus vaccine may induce the human immune system to produce more diversed antibodies and immune memory for a plurality of the antigens.

Since it is less likely that a plurality or most of antigens of the virus would mutate simultaneously, the killed or inactivated virus vaccine is much less likely to lose its effectiveness against variants of virus, comparing to the mRNA vaccine in the long term. As such, the inactivated virus vaccine may prevent new variants from causing infections and future pandemics. In daily practice, however, both the mRNA and inactivated virus vaccine are not as effective as expected.

With respect to certain antigens, when a large quantity of the antigen is introduced into the immune system, it may overwhelm and suppress the immune response. In addition, a second stimulation of the immune system with the same antigen/vaccine produces a significantly stronger immune reaction as compared to a single dose antigen/vaccine, the so-called secondary immune reaction. In light of these, the present invention shows that a higher second/follow-up dose of the vaccine introduced after a first priming dose, which has a lower dose comparing to the second/follow-up dose, creates more potent and more protective effects against the antigen.

To improve the efficacy and/or effectiveness of vaccine, the present invention discloses a new vaccine administering method which administers a low priming dose of a vaccine on Day 1, followed by a higher dose or doses in short time intervals, spanning between Day 2-28. Such a method improves the efficacy and/or effectiveness of the vaccine and prevents severe infection by the virus in humans.

In one embodiment of the invention, a first priming dose of approximately 5% of the full strength dose is administered to a subject on Day 1. In yet another embodiment, a first priming dose of approximately 10% of the full strength dose is administered to a subject. In yet another embodiment of the invention, a first priming dose of approximately 15% of the full strength dose is administered to a subject on Day 1. In yet another embodiment of the invention, a first priming dose of approximately 20% of the full strength dose is administered to a subject on Day 1. In yet another embodiment of the invention, a first priming dose of approximately 25% of the full strength dose is administered to a subject on Day 1. In yet another embodiment of the invention, a first priming dose of approximately 30% of the full strength dose is administered to a subject on Day 1. In yet another embodiment of the invention, a first priming dose of approximately 35% of the full strength dose is administered to a subject on Day 1. In yet another embodiment of the invention, a first priming dose of approximately 40% of the full strength dose is administered to a subject on Day 1. In yet another embodiment of the invention, a first priming dose of approximately 45% of the full strength dose is administered to a subject on Day 1. In yet another embodiment of the invention, a first priming dose of approximately 50% of the full strength dose is administered to a subject on Day 1.

In one embodiment of the invention, a second dose is administered on approximately a middle day which approximately equally divides the time span between the first day and the final day of the administering schedule. In one embodiment of the invention, the second dose is administered on Day 14. In yet another embodiment, the second does is administered between Day 13-17. In yet another embodiment, the second does is administered between Day 11-19. In yet another embodiment, the second does is administered between Day 9-21. In yet another embodiment, the second does is administered between Day 7-23.

In one embodiment of the invention, the second dose has approximately 40% dosage of the full strength dose. In yet another embodiment, the second dose has approximately 45% dosage of the full strength dose. In yet another embodiment, the second dose has approximately 50% dosage of the full strength dose. In yet another embodiment, the second dose has approximately 55% dosage of the full strength dose. In yet another embodiment, the second dose has approximately 60% dosage of the full strength dose. In yet another embodiment, the second dose has approximately 65% dosage of the full strength dose. In yet another embodiment, the second dose has approximately 70% dosage of the full strength dose. In yet another embodiment, the second dose has approximately 75% dosage of the full strength dose. In yet another embodiment, the second dose has approximately 80% dosage of the full strength dose. In yet another embodiment, the second dose has approximately 85% dosage of the full strength dose. In yet another embodiment, the second dose has approximately 90% dosage of the full strength dose. In yet another embodiment, the second dose has approximately 95% dosage of the full strength dose.

In one embodiment, a final dose is administered on the last day of the administering schedule. In one embodiment of the invention, the final dose is administered on approximately Day 28. In yet another embodiment, the final does is administered on approximately Day 30. In yet another embodiment, the final does is administered on approximately Day 32. In yet another embodiment, the final does is administered on approximately Day 34.

In one embodiment of the invention, the final dose has approximately 100% dosage of the full strength dose. In yet another embodiment, the final dose has approximately 95% dosage of the full strength dose. In yet another embodiment, the final dose has approximately 90% dosage of the full strength dose. In yet another embodiment, the final dose has approximately 85% dosage of the full strength dose. In yet another embodiment, the final dose has approximately 80% dosage of the full strength dose. In yet another embodiment, the final dose has approximately 75% dosage of the full strength dose. In yet another embodiment, the final dose has approximately 70% dosage of the full strength dose.

In one embodiment, a third dose administered between the second dose and final dose. In one embodiment, the second dose and third dose are administered on two separate days which approximately equally divides the time span of the administering schedule into three sections.

In one embodiment of the invention, the third dose has approximately 80% dosage of the full strength dose. In yet another embodiment, the third dose has approximately 75% dosage of the full strength dose. In yet another embodiment, the third dose has approximately 70% dosage of the full strength dose. In yet another embodiment, the third dose has approximately 65% dosage of the full strength dose. In yet another embodiment, the third dose has approximately 60% dosage of the full strength dose. In yet another embodiment, the third dose has approximately 55% dosage of the full strength dose. In yet another embodiment, the third dose has approximately 50% dosage of the full strength dose.

Example 1—Vaccine Administration Method for SARS-CoV-2 Vaccines

In one embodiment of the present invention, the vaccine administration method is applied to vaccines for the Severe acute respiratory syndrome coronavirus 2 (SARS-CoV-2) which has caused global COVID-19 pandemic. The COVID-19 pandemic has led to a worldwide health crisis and devastating economic and social issues. Since the SARS-CoV-2 infects a large population within a short period of time, and has no effective treatment yet, it is essential to control the pandemic early and prevent generation of the virus variants. Vaccines play an important role in avoiding pandemics of the coronavirus and other viruses.

The vaccines currently used for SARS-CoV-2 generally fall into two categories, mRNA vaccine and inactivated virus vaccine. The mRNA vaccine contains mRNA sequences of one or more spike protein of the SARS-CoV-2, while the inactivated virus vaccine contains killed SARS-CoV-2. The mRNA vaccine stimulates the human immune system to produce antibodies and memory against the spike protein(s) of COVID-19, preventing duplication of the virus. It is precisely targeted against the critical spike protein of the SARS-CoV-2 and provides better protection than inactivated virus vaccine. However, the mRNA vaccine may gradually lose its the efficacy and/or effectiveness due to mutation of coronavirus's spike protein. Single chain RNA viruses, like the SARS-CoV-2, are highly prone to mutation. From this perspective, the inactivated vaccine provides a better protection as compared to the mRNA vaccine, because it contains all the antigens which induce body immunoreaction.

The present invention provides a method to improve vaccines' efficacy and/or effectiveness and prevent future pandemics caused by the coronavirus. In current practice, the vaccine from the inactivated virus is less effective than the mRNA vaccine. This discrepancy may be due to that the inactivated virus vaccine introduced too many antigens in a large quantity into the body at one time, overwhelming and suppressing the immune system, leading to inadequate immune reaction. Thus, multiple incremental doses at close time intervals improve immunoreaction to vaccines. Viruses, including the coronavirus, constantly mutate and become pathogenic and contagious to humans.

To address these shortcomings, the present invention proposes to use a low vaccine dose to prime the immune system followed by incremental higher doses to induce better immunoreaction over a well-defined short schedule.

In one embodiment of the invention, a vaccine made from the inactivated virus by SINOPHARM is administered to the subjects according to the vaccine administering method of the present invention. The SINOPHARM vaccine's full-strength dose is 600 SU. Therefore, a first dose of the SINOPHARM vaccine contains approximately 10-25% of the full-strength dose, which is about 60-150 SU. A second contains approximately 50% of the full-strength dose, which is about 300 SU.

In one embodiment of the invention, an mRNA vaccine (Pfizer, Comirnaty) is administered to the subjects according to the vaccine administering method of the present invention. The mRNA's full-strength dose is 100 units. Therefore, a first priming dose of the mRNA vaccine contains approximately 10-25% of the full-strength dose, which is about 10-25 units. A second contains approximately 50% of the full-strength dose, which is about 50 units.

The present invention is tested in the manner described below. All subjects are healthy adults who have not been infected with COVID-19 and are divided into three groups. The vaccine used is SINOPHARM's BBIBP-CorV vaccine.

Incremental dose group: the subjects receive a first priming dose of approximately 10% of the full-strength dose on Day 1, followed by a second dose having approximately 50% of the full-strength dose on Day 14, and a final dose having full-strength dose on Day 28, as shown in FIG. 1.

Figure 2:
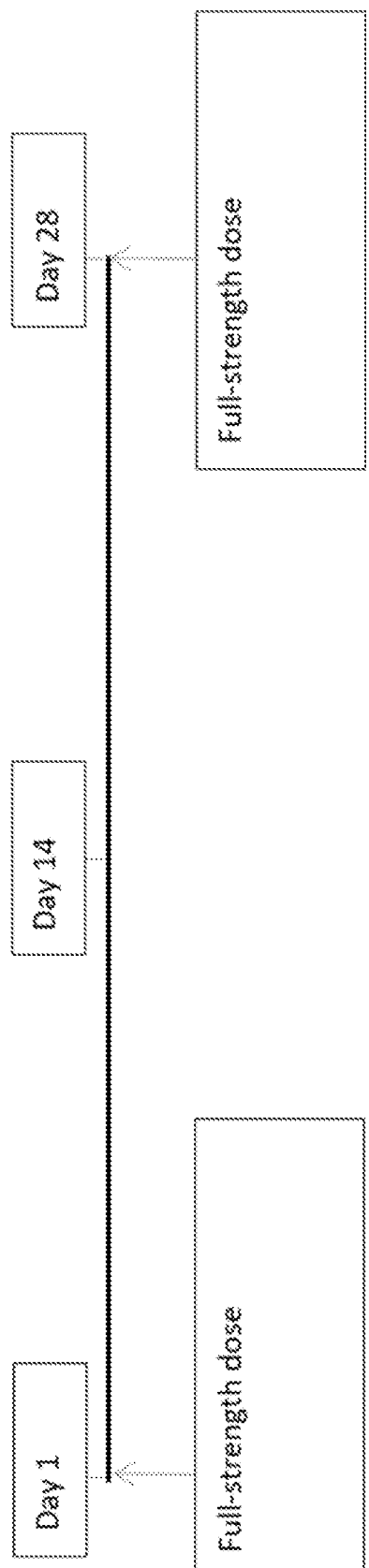
FIG. 2 illustrates a full-strength dose schedule of SINO-PHARM's BBIBP-CorV vaccine.

Full-strength dose group: the subjects receive two full-strength doses of vaccine, one full-strength dose on Day 1 and one full-strength dose on Day 28, as shown in FIG. 2.

Figure 3:
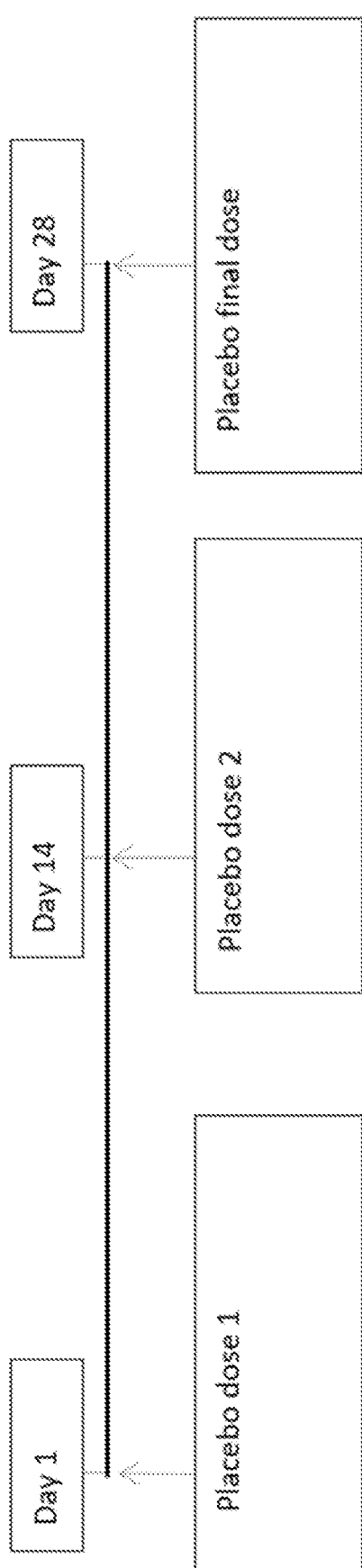
FIG. 3 illustrates a placebo dose schedule.

Placebo group: the subjects receive placebo on Day 1, Day 14, and Day 28, as shown in FIG. 3.

The incremental dose group (group 1) produces the most vigorous immune response. The placebo group has no immune response at all. The full-strength dose group (group 2) responds less than the incremental dose group.

Antibody titer is measured on Day 1 before the first dose, on Day 14 (before the second dose if there is one), on Day 28 before any dosing in each of the three groups, and thereafter on day 60 and day 90. The incremental dose group shows a more robust immune response, meaning significantly greater antibody titer, compared to the other two groups, throughout the test period.

In one embodiment, the priming dose may be 10-25% of the maximum dose.

In another embodiment, the second dose in the incremental dose group may be 45-55% of the maximum dose.

REFERENCES

1. Kathy Katellaf, *Omicron, Delta, Alpha, and More: What To Know About the Coronavirus Variants*. YALE MEDICINE (Mar. 30, 2022), www.yalemedicine.org/news/covid-19-variants-of-concern-omicron.
2. Jason P. Block et al., *Covid-19 Vaccine Effectiveness against the Omicron (B.1.1.529) Variant:*71 MORBIDITY AND MORTALITY WEEKLY REPORT EARLY RELEASE (2022).
3. Nick Andrews et al., *Covid-19 Vaccine Effectiveness against the Omicron (B.1.1.529) Variant.* 386 N. Engl. J. Med. 1532-1546 (2022).
4. Michelle Roberts, *Oxford/AstraZeneca Covid vaccine 'dose error'explained*, BBC NEWS (Nov. 27, 2020, www.bbc.com/news/health-55086927).
5. WHY IS A SECOND BOOSTER OF AN MRNA VACCINE AVAILABLE TO PEOPLE WHO PREVIOUSLY RECEIVED THE JOHNSON & JOHNSON COVID-19 VACCINE?faqs.in.gov/hc/en-us/articles/5352422912148, Apr. 5, 2022
6. TAK W. MAK & MARY E. SAUNDERS, VACCINES AND CLINICAL IMMUNIZATION: THE IMMUNE RESPONSE, 695-749, (1$^{st}$ ed. 2006).

What is claimed is:

1. A method for enhancing an immune response to a coronavirus in a subject, comprising:
   (1) administering to the subject a first dose of a coronavirus vaccine in the amount of 10-25% of the vaccine's full-strength dose on Day 1 of an administering schedule;
   (2) administering to the subject a second dose of the coronavirus vaccine in the amount of 45-55% of the vaccine's full-strength between Day 4-22 of the administering schedule; and
   (3) administering to said subject a final dose of the coronavirus vaccine in the amount of 80-100% of said vaccine's full-strength on the last day of the administering schedule;
      wherein the immune response produced in the subject is stronger than, and/or lasts longer than the immune response produced in the subject if the full-strength dose is given two or three times over the same length of time of the administering schedule.

2. The method according to claim 1, wherein the coronavirus is severe acute respiratory syndrome coronavirus 2 (SARS-COV-2).

3. The method according to claim 2, wherein the coronavirus vaccine is an inactivated virus vaccine.

4. The method according to claim 2, wherein the coronavirus vaccine is an mRNA vaccine.

5. The method according to claim 1, wherein the administering schedule lasts about 24-32 days.

6. The method according to claim 5, wherein the administering schedule lasts 28 days.

7. The method according to claim 6, wherein the second dose is administered on Day 14 of the administering schedule, and the final dose is administered on Day 28 of the administering schedule.

8. The method according to claim 1, wherein a third dose is administered between the second dose and the final dose, and wherein the third dose contains approximately about 50-70% of the vaccine's full-strength dose.

9. The method according to claim 8, wherein the second dose and the third dose are administered on two separate days which equally divide the time period between the Day 1 and last day of the administering schedule.

10. The method according to claim 1, wherein the first dose contains 10% of said vaccine's full-strength dose.

11. The method according to claim 1, wherein the second dose contains 50% of said vaccine's full-strength dose.

12. The method according to claim 1, wherein the final dose contains 100% of said vaccine's full-strength dose.

13. A method for enhancing an immune response to SARS-COV-2 in a subject, comprising:
   (1) administering to the subject a first dose of a SARS-COV-2 vaccine in the amount of 10% of the vaccine's full-strength dose on Day 1 of an administering schedule;
   (2) administering to the subject a second dose of the SARS-COV-2 vaccine in the amount of 50% of the vaccine's full-strength on about Day 14 of the administering schedule; and
   (3) administering to said subject a final dose of the SARS-COV-2 vaccine in the amount of 100% of said vaccine's full-strength on the Day 28 of the administering schedule;
   wherein the immune response produced in the subject is stronger than, and/or lasts longer than the immune response produced in the subject if the full-strength dose is given two or three times over the same length of time of the administering schedule;
   wherein the SARS-COV-2 vaccine is an inactivated virus vaccine.

* * * * *